United States Patent [19]
Menard

[11] Patent Number: 4,761,514
[45] Date of Patent: * Aug. 2, 1988

[54] TOLUENE DISPROPORTIONATION PROCESS

[75] Inventor: Kevin P. Menard, Big Spring, Tex.

[73] Assignee: Cosden Technology, Inc., Dallas, Tex.

[*] Notice: The portion of the term of this patent subsequent to May 12, 2004 has been disclaimed.

[21] Appl. No.: 51,493

[22] Filed: May 18, 1987

[51] Int. Cl.$^4$ ............................................. C07C 3/62
[52] U.S. Cl. ................................................ 585/475
[58] Field of Search ..................................... 585/475

[56] References Cited

U.S. PATENT DOCUMENTS

| | | | |
|---|---|---|---|
| 2,385,524 | 9/1945 | Mattox | 585/474 |
| 3,436,174 | 4/1969 | Sand | 23/113 |
| 3,476,821 | 11/1969 | Brandenburg et al. | 260/672 |
| 3,480,539 | 11/1969 | Voorhies | 208/111 |
| 3,780,122 | 12/1973 | Pollitzer | 260/672 |
| 3,780,123 | 12/1973 | Suggitt | 260/672 |
| 4,300,012 | 11/1981 | Tu et al. | 585/475 |
| 4,665,258 | 5/1987 | Butler et al. | 585/475 |

OTHER PUBLICATIONS

Kirk-Othmer, Encyclopedia of Chemical Technology, 3rd Edition, John Wiley & Sons, 1981, vol. 11, pp. 270-272.
Kirk-Othmer, Encyclopedia of Chemical Technology, 3rd Edition, John Wiley & Sons, 1981, "Molecular Sieves," vol. 15, pp. 638-643.
Bhavikatti et al, "Toluene Disproportionation over Aluminum-Deficient and Metal-Loaded Mordenites. 1. Catalytic Activity and Aging," Ind. Eng. Chem. Prod. Res. Dev., 1981, 20, 102-105.

*Primary Examiner*—Curtis R. Davis
*Attorney, Agent, or Firm*—John K. Abokhair; Mark A. Montgomery; William D. Jackson

[57] ABSTRACT

A process for the disproportionation of a toluene feedstock containing ethylbenzene over an aluminum deficient mordenite catalyst. The mordenite catalyst has a silica/alumina mole ratio of at least 30. The feedstock contains at least 5 wt. % ethylbenzene. Hydrogen is supplied to the disproportionation reactor zone along with the toluene feedstock.

10 Claims, 1 Drawing Sheet

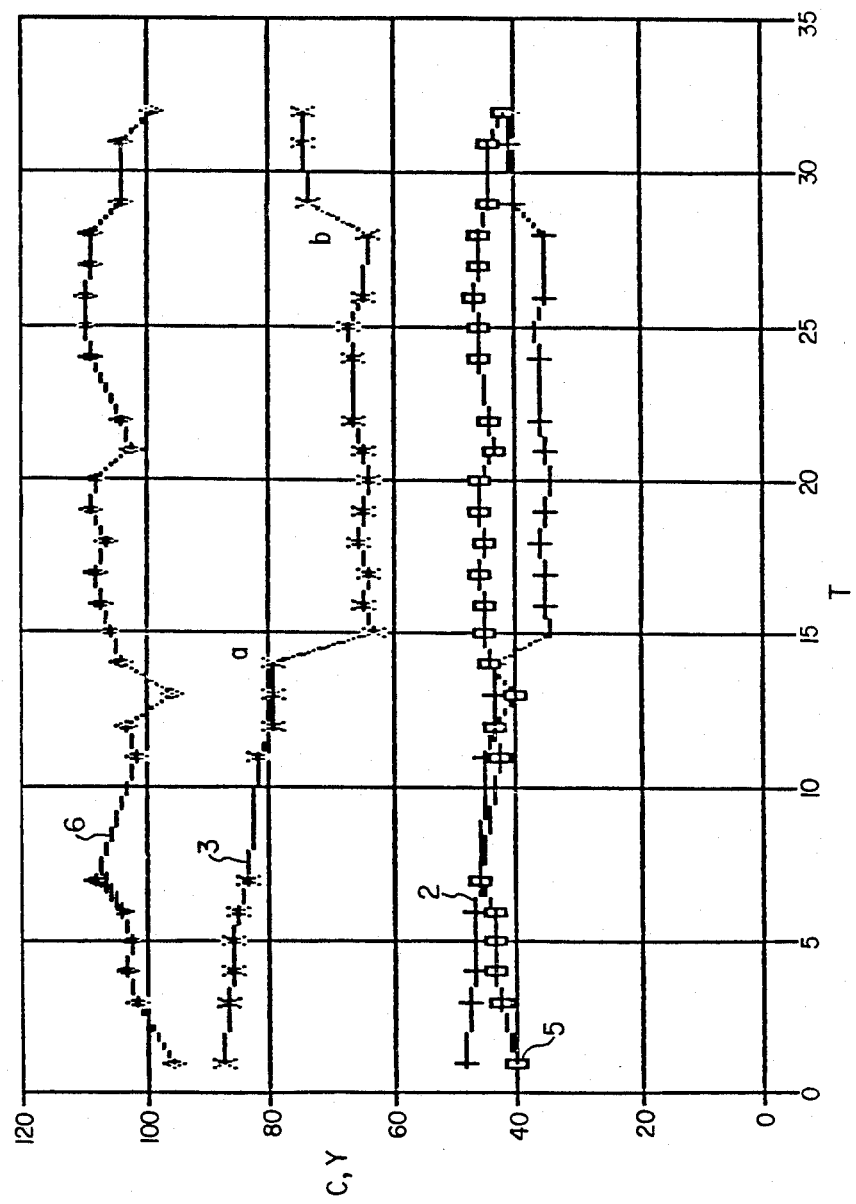

TOLUENE DISPROPORTIONATION PROCESS

TECHNICAL FIELD

This invention relates to the disproportionation of alkylaromatic feedstreams and more particularly to the disproportionation of toluene containing feedstocks of high ethylbenzene content over mordenite catalysts of low aluminum content.

ART BACKGROUND

The disproportionation of toluene involves a well known transalkylation reaction in which toluene is converted to benzene and xylene in accordance with the following reaction:

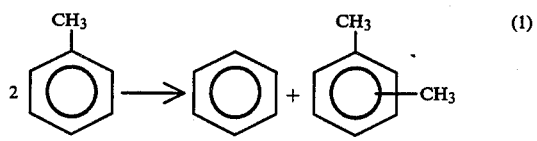

Reaction (1) is mildly exothermic.

Reactions analagous to reaction (1) occur in the disproportionation of higher alkylbenzenes such as ethylbenzene, cumene, and N-propylbenzene. The tendency of alkylbenzenes to disproportionate in general increases with the number of carbon atoms in the alkyl substituents, as indicated by Kirk-Othmer, "Encyclopedia of Chemical Technology," Third Edition, 1981, Vol. 11, pages 270-272. Thus, ethylbenzene disproportionates more readily than toluene, and propylbenzenes disproportionate more readily than ethylbenzene.

Mordenite is one of a number of catalysts commonly employed in the transalkylation of alkylaromatic compounds. Mordenite is a crystalline aluminosilicate zeolite having a network of silicon and aluminum atoms interlinked in its crystalline structure through oxygen atoms. For a general description of mordenite catalysts, reference is made to Kirk-Othmer "Encyclopedia of Chemical Technology", 3rd Edition, 1981, under the heading "Molecular Sieves", Vol. 15, pages 638-643. Mordenite, as found in nature or as synthesized, typically has a relatively low silica to alumina mole ratio of about 10 or less. Such conventionally structured mordenite catalysts are commonly employed in the disproportionation of toluene. However, mordenite catalysts having substantially lower alumina content are also employed in the disproportionation of toluene.

The aluminum deficient mordenite catalysts have a silica/alumina ratio greater than 10 and may sometimes range up to about 100. Such low alumina mordenites may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al.

U.S. Pat. No. 3,780,122 to Pollitzer discloses the transalkylation of toluene using a mordenite zeolite having a silica/alumina ratio greater than 10 which is obtained by acid extraction of a mordenite zeolite having a silica/alumina ratio of less than 10. The silica/alumina ratio may range up to about 100 and preferably is at least about 15. The yield in the Pollitzer process is severely affected by water in the toluene feedstock. Even a very small amount of water (15 ppm) reduces toluene conversion substantially and the patent designates an upper limit of 25 ppm water in the feedstock.

The disproportionation of toluene feedstocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art indicates that while relatively high temperatures can be employed for the high aluminum mordenites (low silica to alumina ratios) somewhat lower temperatures should be employed for the low alumina mordenites. Thus, where mordenite catalysts having high silica/alumina ratios have been employed in the transalkylation of alkylaromatics, it has been the practice to operate toward the lower end of the temperature range. It is also a common practice in this case to promote the catalyst with a catalytically active metallic content. For example, U.S. Pat. No. 3,476,821 to Brandenburg et al discloses disproportionation reactions employing mordenite catalysts having a silica/alumina ratio within the range of 10-100 and preferably within the range of about 20-60. Here the desired temperature ranges are said to be from about 400°-750° F. and preferably 450°-640° F. Metal promoters are said to substantially increase activity and catalyst life.

It is conventional practice to supply hydrogen along with toluene to the reaction zone. While the disproportionation reaction (1) is net of hydrogen, the use of a hydrogen co-feed is generally considered to prolong the useful life of the catalyst, as disclosed, for example, in the above patent to Brandenburg. The amount of hydrogen supplied, which normally is measured in terms of the hydrogen/toluene mole ratio, is generally shown in the prior art to increase as temperature increases. For example, while the patent to Pollitzer discloses a range for the hydrogen/toluene mole ratio of 2-20 corresponding to the broad temperature range of 200°-480° C., the specific examples in Pollitzer of operating at temperatures ranging from 300°-400° C. employ a hydrogen/toluene mole ratio of 10.

Bhavikatti et al, "Toluene Disproportionation over Aluminum-Deficient and Metal-Loaded Mordenites. 1. Catalytic Activity and Aging", Ind. Eng. Chem. Prod. Res. Dev. 1981, 20, 102-105, discloses toluene disproportionation at 400° C. over mordenite catalysts of silica/alumina mole ratios of 12, 16, 23, 32, and 61. The tests reported in Bhavikatti were carried out at atmospheric pressure and with a WHSV of 1. As the silica/alumina mole ratio is increased, catalyst activity substantially decreased while aging quality increased. That is, the aging rates were lower. Based upon short term aging studies, the best silica/alumina mole ratio appeared to be 23. Catalyst decay was also supressed by loading the mordenite with nickel.

U.S. patent application Ser. No. 826,848, now U.S. Pat. No. 4,665,258, filed Feb. 6, 1986, by James R. Butler and Kevin P. Menard discloses disproportionation of a toluene containing feedstock employing an aluminum deficient mordenite catalyst under relatively severe disproportionation conditions. The mordenite catalyst has a silica/alumina mole ratio of at least 30 and preferably a silica/alumina ratio within the range of 40-60. The feedstock may be supplied to a reaction zone containing the mordenite catalyst at rates providing relatively high space velocities. The toluene weight hourly space velocity (WHSV) may be greater than 1. Hydrogen is also supplied to the reaction zone at a rate to provide a hydrogen/toluene mole ratio within the range of 3-6. The reaction zone is operated at a temperature in the range of 370°-500° C. and a hydrogen pressure of at least 500 psig to effect disproportionation of the toluene to benzene and xylenes. More specific reaction conditions include a temperature within the range of 400°-480° C., a hydrogen pressure of about 600-800 psig, and a mole ratio of hydrogen to toluene of about 4. The preferred catalyst is hydrogen mordenite having a silica/alumina ratio of about 48.

As indicated previously, other alkyl aromatic compounds are known to undergo disproportionation and aluminum deficient mordenites such as described above can be used in the catalysis of such reactions. For example, the aforementioned patent to Brandenburg includes as alkyl aromatic hydrocarbons subject to the disclosed disproportionation process, alkylbenzenes having one to three $C_1$-$C_4$ alkyl groups and methylnaphthalene. Brandenburg specifically gives examples of the disproportionation of toluene and the disproportionation of ethylbenzene. Brandenburg discloses comparative examples in which toluene and ethylbenzene are disproportionated over aluminum deficient catalysts at respective temperatures of 550° F. and 450° F. In each case, the silica/alumina ratio of the mordenite catalyst was 24:1. Consistent with the aforementioned disclosure in Kirk-Othmer regarding the increased tendency of the higher alkylbenzenes to disproportionate, the ethylbenzene underwent a higher degree of disproportionation than the toluene notwithstanding the lower temperature employed in the ethylbenzene disproportionation reaction.

While disproportionation reactions of the higher alkylbenzenes are known, as discussed above, the prior art does not suggest the use of aluminum deficient mordenite catalyst in the disproportionation of toluene feedstocks containing ethylbenzene in more than trace amounts, typically about 1% or less. In fact, the prior art teaches the contrary; that feedstocks containing substantial quantities of both toluene and ethylbenzene should not be employed in such disproportionation reactions. Thus, the aforementioned patent to Pollitzer, which discloses the disproportionation of toluene or ethylbenzene, but not both in the same feedstock, requires that an organic chloride containing compound, specifically tertiary butyl chloride, be added to the feedstock in the case of ethylbenzene. Yet, another reference involving the use of aluminum deficient mordenites in the disproportionation of ethylbenzene or $C_3+$ alkylbenzenes, specifically excludes the presence of toluene or other methyl substituted benzenes. Thus, U.S. Pat. No. 3,780,123 to Suggitt, which discloses the use of acid leached mordenites and gives examples of those with silica/alumina ratios 40/1 to 65/1 composited with sulfided metals, specifically requires that the feedstock contain only non-methyl alkylbenzenes.

DESCRIPTION OF THE INVENTION

In accordance with the present invention, there is provided a new and improved process for the disproportionation of a toluene feedstock over an aluminum deficient mordenite catalyst in which the feedstock has a substantial ethylbenzene content. In carrying out the invention, a toluene containing feedstock is supplied to a reaction zone containing a mordenite catalyst having a silica/alumina ratio of at least 30. Hydrogen is also supplied to the reaction zone to provide a hydrogen environment. The feedstock contains at least 5 wt. % ethylbenzene, and the reaction zone is operated under temperature and pressure conditions to effect the disproportionation of toluene and ethylbenzene to benzene, xylene, ethyltoluene and di-ethylbenzene. The disproportionation product containing these compounds is withdrawn from the reaction zone. Preferably, the reaction zone is operated at a temperature within the range of 370°-500° C. The gas make resulting from the toluene and ethylbenzene conversion reactions is less than 0.5 wt. %, and usually less than 0.1 wt. %.

BRIEF DESCRIPTION OF THE DRAWING

The drawing is a graph illustrating toluene conversion and benzene yield in a disproportionation process carried out over an aluminum deficient mordenite catalyst in which ethylbenzene is added to the toluene feedstock.

BEST MODES FOR CARRYING OUT THE INVENTION

As noted previously, the aforementioned application Ser. No. 826,848 by Butler et al represents a substantial departure from practices previously followed in disproportionating toluene feedstocks over aluminum deficient mordenite catalysts. The present invention provides yet a further departure from such prior art practices in that the feedstock contains a substantial quantity of ethylbenzene which undergoes disproportionation over a high silica/alumina ratio mordenite catalyst as disclosed in the Butler et al application. The majority of the ethylbenzene in the feedstream is converted to benzene and $C_9+$ aromatics, principally ethyltoluene and di-ethylbenzene. This is accomplished without substantial deethylation or hydrodeethylation leading to ethylene or ethane in the gaseous effluent from the disproportionation reactor.

Except for the inclusion of ethylbenzene in the toluene feedstock, the present invention may be carried out in accordance with the process parameters and procedures described in the aforementioned Butler et al application. Thus, the reaction zone is normally operated at a temperature within the range of 370°-500° C. and preferably within the range of 380°-480° C. The mordenite catalyst employed in the present invention should have a silica/alumina ratio of at least 30 and preferably within the range of 40-60. The catalyst need not be promoted or otherwise modified with metal promoters such as disclosed in the patent to Brandenburg or with sulfided components as disclosed in the patent to Suggitt. Nor is it necessary or desirable to incorporate organochloride compounds, such as the tertiary butylchloride disclosed in the patent to Pollitzer, in the feedstream. As discussed below, codisproportionation of substantial quantities of ethylbenzene along with toluene in the feedstream is accomplished using the aluminum deficient mordenite catalyst which is otherwise unmodified. This is accomplished without any significant increase in the gas make from the disproportionation unit. Hydrogen is normally also supplied to the reaction zone to provide a hydrogen pressure within the zone of at least 500 psig. Unless indicated otherwise, all pressures given herein are hydrogen pressures or, in the case of a hydrogen feed containing other gases, hydrogen partial pressures. For example, in the case of a gas containing 90% hydrogen and 10% other gases such as light hydrocarbons and nitrogen, the reaction zone should be operated at a pressure of about 555 psig to yield a hydrogen presure of 500 psig. The pressure at which the disproportionation reaction is carried out normally will be within the range of about 600–800 psig. Lower pressures may be employed, but will result in lower toluene conversion unless higher temperatures are used, which will decrease the catalyst cycle life. Preferably, the reaction zone for the toluene disproportionation reaction will be at a pressure of about 600 psig or above.

The aforementioned temperature and pressure conditions permit the use of lower than normal hydrogen amounts and higher than normal space velocities. The specific parameters employed in this regard include an alkylbenzene (toluene and ethylbenzene) space velocity (WHSV) in excess of 1 hr$^{-1}$ and a hydrogen/alkylbenzene mole ratio within the range of 3–6. Typical space velocities (WHSV) will range from about 1.3 to about 3 hr$^{-1}$.

As further described in the a forementioned Butler et al application, a hot inert gas such as hydrogen may be used in a preflush procedure in order to dehydrate the mordenite catalyst and remove water which is believed to function within the catalyst framework to block active sites. The preflush may be carried out with gas heated to a temperature of about 400° C. and continued for a period of one day or more. As also noted in the Butler et al application, the toluene feed may contain water in excess of the 15 ppm concentration indicated by the aforementioned patent by Pollitzer to be unsatisfactory, and well above the 25 ppm upper limit disclosed by Pollitzer. Thus, water concentrations ranging from about 50 ppm up to 250 ppm (saturation) encountered in toluene feedstocks under ambient conditions can be tolerated. For a further description of the process parameters and procedures which may be employed in toluene disproportionation processes conducted in accordance with the present invention, reference is made to the aforementioned application Ser. No. 826,848 to Butler et al, the entire disclosure which is incorporated herein by reference.

As noted previously, ethylbenzene is more readily transalkylated than toluene. Accordingly, as indicated by the aforementioned patent to Brandenburg, where toluene and ethylbenzene feedstocks are separately subjected to disproportionation reactions, the ethylbenzene reaction is carried out under less severe reaction conditions. Thus, under the same reaction conditions involving the higher temperatures normally used for toluene disproportionation, as the temperature is increased one would expect that the ethylbenzene conversion reaction would tend to shift away from the disproportionation regime toward dealkylation or hydrodealkylation. In addition, as taught, for example, in Rabo, J., "Zeolite Chemistry and Catalysis" ACS Monograph: 171, American Chemical Society 1976, Washington, D.C., pages 696–697, acid extraction of mordenite to arrive at an increased silica/alumina ratio increases the effective pour diameter of the catalyst, thus changing its shape selective characteristics. One would expect this to favor access of the more bulky ethyl substituted benzene compounds to the active catalyst sites, thus further enhancing ethylbenzene conversion at the expense of the toluene disproportionation reaction, and also favoring deethylation or hydrodeethylation where high temperatures are involved. In fact, when carrying out disproportionation of an ethylbenzene containing toluene feedstock over an aluminum deficient mordenite catalyst in accordance with the present invention, the toluene disproportionation reaction is not adversely affected. Futhermore, even when operating at the relatively high temperature conditions taught by the Butler et al application for toluene disproportionation over the high silica/alumina ratio catalyst, the ethylbenzene is predominantly disproportionated with little or no deethylation or hydrodeethylation.

Ethylbenzene and other aromatic compounds are found in toluene feedstocks. However, ethylbenzene is usually present in only a trace amount of about 1 wt. % or less. For example, nitration grade toluene is about 99.5% pure and contains only a few tenths percent of benzene with even smaller amounts of ethylbenzene and other impurities. In the present invention the feedstock supplied to the disproportionation unit contains at least 5 wt. % ethylbenzene and may have a substantially higher ethylbenzene content. More specifically, the ethylbenzene content may be greater than 10 wt. % and may range up to 50% ethylbenzene (approximately equal parts toluene and ethylbenzene) or even higher. The disproportionation reaction zone contains an aluminum deficient mordenite catalyst, i.e., one having a silica/alumina/mole ratio of at least 30 as described in the aforementioned Butler et al application. Hydrogen co-feed is applied to the reaction zone. The disproportionation product from the reaction zone is principally benzene, xylene, di-ethylbenzene, and ethyltoluene; lesser amounts of unreacted toluene and ethylbenzene; and very small amounts of aromatic and non-aromatic compounds. The gaseous effluent from the reaction zone is primarily hydrogen (and such other inert gases as may be present in the hydrogen co-feed) and very small amounts, if any, of hydrocarbon gases produced in the course of the disproportionation reactions. Specifically $C_2$ gases (ethane or ethylene) are present, if at all, in an amount of less than 0.5 wt. % and usually no more than 0.1 wt. % of the total hydrocarbon product from the reaction zone.

In experimental work respecting the invention, a toluene feedstock was supplied over a prolonged period of time to a reaction zone containing an aluminum deficient mordenite catalyst. The reaction zone was operated at an average temperature of about 470° C. and an average hydrogen pressure of about 600 psig. The hydrogen co-feed was supplied at a rate to provide a hydrogen/hydrocarbon mole ratio of about 4. The catalyst employed in the experimental work was the aluminum deficient mordenite catalyst identified in the aforementioned Butler et al application as catalyst C and having a silica/alumina mole ratio of 48. Analyses of samples of the toluene feedstock and the disproportionation product taken during the initial two weeks of operation are set forth in Table I.

TABLE I

|  | Feed wt % | Product wt % |
| --- | --- | --- |
| Non-Aromatic | 0.43 | .2 |
| Benzene | 2.21 | 22 |
| Toluene | 97.08 | 49.8 |
| Ethylbenzene | 0.26 | .8 |
| Para-xylene | 0.0 | 4.8 |
| Ortho-xylene | 0.0 | 5.1 |
| Meta-xylene | 0.01 | 11.8 |
| C9+ | 0.02 | 1.7 |
| Meta-ethyl toluene | — | .5 |
| Para-ethyl toluene | — | .3 |
| Ortho-ethyl toluene | — | .1 |
| 1,3,5 Tri-ethylbenzene | — | .7 |
| 1,2,4 Tri-ethylbenzene | — | 1.9 |

TABLE I-continued

| | Feed wt % | Product wt % |
|---|---|---|
| 1,2,3 Tri-ethylbenzene | — | .3 |

On day 14, a new feedstock containing 10% by weight ethylbenzene and 90% of the original feedstock was made to provide composite toluene-ethylbenzene feed to the reaction zone of about 90% toluene and 9% ethylbenzene. The reaction zone temperature and pressure and the hydrogen co-feed remained the same as before. The ethylbenzene feed was continued for about 14 days. Feed and product analyses of samples taken during this period are set forth in Table II.

TABLE II

| | Feed wt % | Product wt % |
|---|---|---|
| Non-Aromatic | .71 | .2 |
| Benzene | 2.61 | 21.9 |
| Toluene | 87.70 | 50.7 |
| Ethylbenzene | 9.10 | 2.9 |
| Para-xylene | 0 | 3.8 |
| Ortho-xylene | .02 | 4.2 |
| Meta-xylene | .01 | 9.7 |
| C$_9$+ | .02 | 1.6 |
| Meta-ethyl toluene | — | 1.6 |
| Para-ethyl toluene | — | 1 |
| Ortho-ethyl toluene | — | .4 |
| 1,3,5 Tri-ethylbenzene | — | .5 |
| 1,2,4 Tri-ethylbenzene | — | 1.3 |
| 1,2,3 Tri-ethylbenzene | — | .2 |

As indicated by the data of Table II, about 70% of the ethylbenzene in the feedscreen was converted without adversely impacting upon the toluene disproportionation reaction. Further, notwithstanding the relatively high temperature employed in the experimental work, substantially no dealkylation or hydrodealkylation of the ethylbenzene occurred.

On day 28 of the test, the ethylbenzene feed was terminated to return the feedstock to the condition prior to initiation of the ethylbenzene feed. The experimental run was continued for an additional five days. Analyses of a feedstock sample and disproportionation product sample taken during this last stage of the experiment are set forth in Table III.

TABLE III

| | Feed wt % | Product wt % |
|---|---|---|
| Non-Aromatic | 0.43 | 0.2 |
| Benzene | 2.21 | 18.6 |
| Toluene | 97.08 | 56.4 |
| Ethylbenzene | .26 | 0.6 |
| Para-xylene | 0 | 4.4 |
| Ortho-xylene | 0 | 4.8 |
| Meta-xylene | .01 | 11.2 |
| C$_9$+ | .02 | 0.9 |
| Meta-ethyl toluene | — | 0.4 |
| Para-ethyl toluene | — | 0.3 |
| Ortho-ethyl toluene | — | 0.1 |
| 1,3,5 Tri-ethylbenzene | — | 0.5 |
| 1,2,4 Tri-ethylbenzene | — | 1.4 |
| 1,2,3 Tri-ethylbenzene | — | 0.2 |

The drawing is a graph of toluene conversion, C, and benzene yield, Y, in percent plotted on the ordinate versus the time T, in days on the abscissa for the experimental procedure described above. In the drawing, curve 2 is a graph of absolute toluene conversion expressed as a percentage of toluene in the feed, and curve 3 shows the toluene conversion expressed as the percentage of total theoretical toluene conversion. Curve 5 is a graph of benzene yield in the disproportionation product (the weight % of benzene in the product). Curve 6 is a graph of the benzene yield expressed as a percentage of the total possible benzene yield. Reference a in the drawing illustrates the point at which ethylbenzene feed was initiated and reference b the point at which it was terminated.

The drawing indicates a reduction in toluene conversion and an increase in benzene yield during the time that feedstock included ethylbenzene. However, the reduction in toluene conversion is a mathematical artifact due to the fact that while the total feed volume remained the same in an absolute sense, the percent of toluene in the system decreased from near 100% to about 90% upon the addition of the ethylbenzene. More importantly, it can be seen from an examination of the drawing that the inclusion of ethylbenzene caused no decrease in catalyst activity or aging quality. In this respect, curves 2 and 5 show the expected gradual decrease in toluene conversion with time. Upon conclusion of the ethylbenzene feed, the toluene conversion returned to the level as would be indicated by a projection of the conversion data over the first two weeks of the test.

Where the feedstock contains substantially more ethylbenzene than in the herein described experimental data, the amount of C$_9$+ aromatic compounds in the feedstock would, of course, increase substantially. However, this may be utilized to advantage in the production of a high octane product usable as a blend stock for gasoline. Thus, based upon the above described experimental work, a 50/50 toluene/EB feedstream would be expected to produce a product having about 20% benzene, 22% ethylbenzene, 26% toluene, 12% xylenes and 20% ethyltoluene, diethlybenzene and other heaves together. Upon the removal of benzene, the remaining disproportionation product would provide a high octane gasoline blend having a relatively wide boiling point range in the gasoline range.

To take advantage of this relationship, a toluene feedstock having a substantial ethylbenzene content of 10 wt. % or more is supplied to a disproportionation unit operated in accordance with the present invention and the output then supplied to a suitable separation zone, such as a fractionation column, for the removal of benzene. The residual output from the benzene column having a boiling point range of about 82°-205° C. can then be applied to a gasoline blending process. If it is desired to recycle the toluene, a second fractionation column downstream from the benzene column can be employed. Here, the overhead from the second column containing toluene is recycled to the feedstreams supplied to the disproportionation unit and the residual fraction having a boiling point range of about 112°-205° C. then applied to the gasoline blending station.

Having described specific embodiments of the present invention, it will be understood that modification thereof may be suggested to those skilled in the art, and it is intended to cover all such modifications as fall within the scope of the appended claims.

I claim:

1. In a process for the disproportionation of a toluene and ethylbenzene containing feedstock to produce a disproportionation product containing benzene, xylene and ethylated aromatics, the steps comprising:

(a) supplying said feedstock in which ethylbenzene is present in a concentration of at least 5 wt. % to a reaction zone into contact with a mordenite catalyst within said reaction zone having a silica/alumina mole ratio of at least 30;
(b) co-feeding hydrogen to said reaction zone to provide a hydrogen environment therein;
(c) operating said reaction zone under temperature and pressure conditions to effect the disproportionation of toluene and ethylbenzene to benzene, xylene, ethylbenzene and ethyltoluene; and
(d) withdrawing said disproportionation product from said reaction zone.

2. The method of claim 1 wherein said reaction zone is operated at a temperature within the range of 370°–500° C.

3. The method of claim 1 wherein said mordenite catalyst has a silica/alumina mole ratio within the range of 40–60.

4. The method of claim 1 wherein said mordenite catalyst has a silica/alumina mole ratio of about 48.

5. The method of claim 1 wherein the effluent from said reaction zone contains less than 0.5 wt. % $C_2$ hydrocarbon gas of the total hydrocarbon product from said reaction zone.

6. The method of claim 1 wherein the effluent from said reaction zone contains less than 0.1 wt. % $C_2$ hydrocarbon gas of the total hydrocarbon product from said reaction zone.

7. The method of claim 1 wherein the feedstock supplied to said reaction zone contains ethylbenzene in a concentration of at least 10 wt. %.

8. The method of claim 1 further comprising the step of supplying the disproportionation product from said reaction zone to a separation zone and removing benzene from said product at said separation zone.

9. The method of claim 8 wherein the feedstock supplied to said reaction zone contains at least 10 wt. % ethylbenzene.

10. The method of claim 8 further comprising the step of supplying the benzene free product from said separation zone to a second separation zone, within said second separation zone separting toluene from said product, and recycling said toluene to said reaction zone.

* * * * *